United States Patent
Krzysik et al.

(10) Patent No.: US 6,440,437 B1
(45) Date of Patent: Aug. 27, 2002

(54) WET WIPES HAVING SKIN HEALTH BENEFITS

(75) Inventors: Duane Gerard Krzysik; Beth Anne Lange; David Roland Otts; Brenda Marie Nelson, all of Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/491,898

(22) Filed: Jan. 24, 2000

(51) Int. Cl.[7] ............................. A61K 9/00; A61K 9/70; A61F 13/00
(52) U.S. Cl. ..................... 424/402; 424/400; 424/443
(58) Field of Search ................................ 424/400, 402, 424/443

(56) References Cited

U.S. PATENT DOCUMENTS

| | | | |
|---|---|---|---|
| 3,896,807 A | 7/1975 | Buchalter | 128/261 |
| 4,100,324 A | 7/1978 | Anderson et al. | 428/288 |
| 4,273,786 A | 6/1981 | Kraskin | 424/319 |
| 4,381,782 A | 5/1983 | Mazurak et al. | 604/368 |
| 4,604,281 A | 8/1986 | Deckner et al. | 424/59 |
| 4,604,313 A | 8/1986 | McFarland et al. | 428/172 |
| 4,690,821 A | 9/1987 | Smith et al. | 424/401 |
| 4,704,116 A | 11/1987 | Enloe | 604/385 A |
| 4,798,603 A | 1/1989 | Meyer et al. | 604/378 |
| 4,818,464 A | 4/1989 | Lau | 264/510 |
| 4,842,593 A | 6/1989 | Jordan et al. | 604/360 |
| 4,846,823 A | 7/1989 | Enloe | 604/385.2 |
| 5,019,073 A | 5/1991 | Roessler et al. | 604/391 |
| 5,176,671 A | 1/1993 | Roessler et al. | 604/391 |
| 5,192,606 A | 3/1993 | Proxmire et al. | 428/284 |
| 5,288,546 A | 2/1994 | Roessler et al. | 428/284 |
| 5,304,162 A | 4/1994 | Kuen | 604/391 |
| 5,318,555 A | 6/1994 | Siebers et al. | 604/390 |
| 5,350,624 A | 9/1994 | Georger et al. | 428/219 |
| 5,364,382 A | 11/1994 | Latimer et al. | 604/378 |
| 5,374,262 A | 12/1994 | Keuhn, Jr. et al. | 604/391 |
| 5,386,595 A | 2/1995 | Kuen et al. | 2/400 |
| 5,399,219 A | 3/1995 | Roessler et al. | 156/259 |
| 5,403,302 A | 4/1995 | Roessler et al. | 604/391 |
| 5,405,342 A | 4/1995 | Roessler et al. | 604/364 |
| 5,413,570 A | 5/1995 | Enloe | 604/385.2 |
| 5,415,644 A | 5/1995 | Enloe | 604/385.2 |
| 5,423,789 A | 6/1995 | Kuen | 604/386 |
| 5,429,629 A | 7/1995 | Latimer et al. | 604/378 |
| 5,486,166 A | 1/1996 | Bishop et al. | 604/366 |
| 5,490,846 A | 2/1996 | Ellis et al. | 604/366 |
| 5,508,034 A | 4/1996 | Bernstein | 424/401 |
| 5,509,915 A | 4/1996 | Hanson et al. | 604/378 |
| 5,599,338 A | 2/1997 | Enloe | 604/385.2 |
| 5,643,588 A | 7/1997 | Roe et al. | 424/402 |
| 5,643,899 A | 7/1997 | Elias et al. | 514/171 |
| 5,648,083 A | * 7/1997 | Blieszner et al. | 424/402 |
| 5,651,862 A | 7/1997 | Anderson et al. | 162/127 |
| 5,653,970 A | * 8/1997 | Vermeer | 424/70.24 |
| 5,656,278 A | 8/1997 | Enjolras | 424/401 |
| 5,674,511 A | 10/1997 | Kacher et al. | 424/401 |
| 5,738,859 A | 4/1998 | Posner | 424/401 |
| 5,744,145 A | 4/1998 | Bertoli et al. | 424/401 |
| 5,800,818 A | 9/1998 | Prugnaud et al. | 424/195.1 |
| 5,849,315 A | 12/1998 | Rerek et al. | 424/401 |
| 5,863,663 A | 1/1999 | Mackey et al. | 428/486 |
| 5,869,070 A | 2/1999 | Dixon et al. | 424/401 |
| 5,968,025 A | 10/1999 | Roe et al. | 604/364 |
| 6,118,041 A | 9/2000 | Roe et al. | 604/360 |
| 6,152,906 A | 11/2000 | Faulks et al. | 604/385.01 |

FOREIGN PATENT DOCUMENTS

| | | |
|---|---|---|
| FR | 2 331 980 | 6/1977 |
| GB | 880276 A | 10/1961 |
| WO | WO 97/31620 A2 | 9/1997 |
| WO | WO 99/12519 A1 | 3/1999 |
| WO | WO 99/13861 A1 | 3/1999 |
| WO | WO 99/37744 A2 | 7/1999 |
| WO | WO 99/45973 | 9/1999 |
| WO | WO 99/45974 | 9/1999 |
| WO | WO 99/45976 | 9/1999 |

OTHER PUBLICATIONS

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: E 96–92, "Standard Test Methods for Water Vapor Transmission of Materials," pp. 702–709, published Mar. 1992.

Derwent World Patent Database abstract of DE 4136540: Description of D. Pegaz, "Disposable Diaper."

Feingold, Keneneth R., MD, "Permeability Barrier Homeostasis: Its Biochemical Basis and Regulation," Cosmetics & Toiletries, vol. 112, Jul. 1997, pp. 49, 50, 53–59.

Fluhr, J.W. et al., "Glycerol Accelerates Recovery of Barrier Function In Vivo," Acta Derm, Venereol, 1999; 79: pp. 418–421.

Ghadially, Ruby, MD, et al., "Effects of petrolatum on stratum corneum structure and function," Journal of the American Academy of Dermatalogy, vol. 26, No. 3, Mar. 1992, pp. 387–396.

Yang, L. et al., "Topical Stratum Corneum Lipids Accelerate Barrier Repair After Tape Stripping, Solvent Treatment And Some But Not All Types Of Detergent Treatment," British Journal of Dermatology, vol. 133, No. 5, Nov. 1995, pp. 679–685.

Abstract of Japan 59–227816 A: Description of Kao Corp., "Cleansing Lotions Containing Cholesterol Esters."

* cited by examiner

*Primary Examiner*—Thurman K. Page
*Assistant Examiner*—S. Howard
(74) *Attorney, Agent, or Firm*—Patricia A. Charlier

(57) ABSTRACT

A skin health enhancing soft wet wipe or wipe-type product, such as a baby wipe, an adult wipe, hand wipe, a face wipe, a cosmetic wipe, a household wipe, an industrial wipe, a personal cleansing wipe, cotton balls, cotton tipped swabs, and the like, can be made by combining the wipe or wipe-type product with an oil-in-water emulsion composition comprising a natural fat or oil, sterol or sterol derivative, humectant, emulsifying surfactant, and water.

51 Claims, No Drawings

WET WIPES HAVING SKIN HEALTH BENEFITS

FIELD OF THE INVENTION

The present invention relates to wet wipes and wipe-type products. More particularly, the present invention particularly relates to wet wipes and wipe-type products that can be used for a variety of purposes including cleaning, cosmetics removal, and sanitation comprising an oil-in-water emulsion composition solution that cleans the surface of the skin and provides enhanced skin health benefits.

BACKGROUND OF THE INVENTION

The stratum corneum is the outer-most layer of the skin and is responsible for regulating skin water levels and functioning as a barrier against chemicals and other stressors found in the environment. The complex arrangement of lipids in the intercellular space of the stratum corneum is responsible for the establishment of normal barrier function. Multi-layered structures of cholesterol, ceramides, and fatty acids, as well as some other minor lipids, provide the major barrier to the transport of hydrophillic substances into the or through the skin. The link between the barrier function and skin health can be observed through skin inflammation that results from the extraction of lipids from the skin.

In addition to inflammation, disrupted barrier function can result in a number of skin conditions, most notably, dry skin. Moisturizers that consist of occlusive chemistries or humectants are commonly utilized to treat dry skin.

Diaper dermatitis, in infants and adults, is a genre of skin conditions that, in large part, originate from impaired barrier function. Impairment of the skin barrier can result from a variety of factors, including; increased skin hydration due to the occlusion of the skin caused by diapers, enzymatic skin damage due to fecal and urinary enzymes, physical abrasion caused by diapers, washcloths, and wet wipes, and removal of skin lipids by surfactant associated with bathing and cleaning.

Occlusion of the skin results in an increased skin hydration due to the blocking of evaporative water loss from the surface of the skin. The hydration level of diapered skin may reach between five to ten times that of undiapered skin. Frequent contact of diapered skin with urine may also contribute to increased skin hydration. Increased skin hydration disrupts skin lipid organization in the stratum corneum. This disruption may increase the skin permeability allowing the penetration of irritants from feces and urine into the skin.

Results from studies performed on hairless mice reveals the fecal enzymes, specifically proteases and lipases, are major skin irritants in the diapered skin environment. Fecal proteases degrade the stratum corneum proteins resulting in inflammatory reactions and facilitation of the penetration of low molecular weight irritants. Urine was observed to elevate skin pH thereby facilitating enzymatic action on the skin as well causing inflammatory reactions in the skin.

Diapered skin is typically cleaned by the application of cotton wash cloths or disposable wet wipes. The effect on the skin by the wet wipes depends upon the materials and surfactant systems used for the wipes. Diapered skin is normally cleansed several times a day with wipes utilizing solutions containing surfactants. Surfactants are known to extract lipids from the stratum corneum or disorganize the lipid structure within the stratum corneum, thereby decreasing the barrier function. The wet wipe and wipe-type product material can cause physical abrasion damage to the skin and can lead to an increase in transepidermal water loss, an indication of decreased barrier function. Other instances from which skin barrier function interruption results are frequent hand washing and contact dermatitis originating from harsh surfactants and other chemical irritants.

Once the skin barrier has been compromised, a series of events occur within the skin to synthesize and organize lipids to restore the barrier function. The body naturally repairs defects in the skin barrier function by increasing the production of key lipids found in the skin, such as cholesterol, ceramides, and fatty acids, and key lipid synthesizing enzymes. Two known environmental conditions inhibit the natural skin barrier repair mechanisms relating to diapered skin. The first condition is a neutral skin pH, and the other condition is the occlusion of the skin. Chronic exposure to feces and urine, as well as the continued occlusion of the skin, therefore, leads to chronic disruption of the skin barrier function.

Wet wipes are well known commercial consumer products that have been available in many forms. Perhaps the most common form of wet wipes has been a stack of moistened sheets that have been packaged in a plastic container. The wet wipes have been made from a variety of materials that have been moistened with a variety of suitable mild surfactant-based solutions. Such wet wipes have been used for baby wipes, hand wipes, household cleaning wipes, industrial wipes, body and facial wipes, and the like.

Typically, such conventional wet wipes have included a single layer of a substantially homogeneous material. For example, conventional wet wipes have included an air laid web of fibers that are uniformly mixed or distributed throughout the web. The wipes have included polymeric fibers such as polyester, polyethylene and polypropylene and natural or synthetic fibers such as cellulosic fibers. Other conventional wet wipes have included a coformed web of polypropylene and cellulosic fibers wherein the fibers are uniformly mixed throughout the web.

However, other forms of a wet wipe or wipe-type product includes a wipe product having a nonwoven, layered basesheet. The layered basesheet may include at least two layers positioned in facing relation with each other wherein one of the layers includes fibers that are not included in the other layer. Such an arrangement may be wherein at least one of the layers includes polyethylene fibers and at least one of the layers includes polypropylene fibers. In alternate forms, the layers may include similar materials, but in differing amounts. The different layers can be configured to provide different physical properties, such as softness, to the wipe product while another layer may be configured to provide other properties, such as strength, to the wipe product.

The balance of physical properties, such as softness, flexibility, strength, integrity and resiliency has not been completely optimized. Topical chemistry may be used to enhance the delivered product properties of the wet wipes and wipe-type products. This has been particularly true for those users desiring improved skin health or the ability to impart skin health benefits. The skin health benefits of the wipe product or the skin health benefits imparted from the wipe product may be perceived to be particularly important for body wipes which are intended for repeated contact the skin of an adult to an infant.

Thus, what is needed in the art are products that help maintain skin barrier function, particularly in the diapered skin environment, such as a wet wipe or wipe-type product that: a) deposits suitable chemistries on the skin to enhance skin barrier; b) minimizes physical damage to the skin due to wiping; c) leaves the skin feeling soft and supple; and, d) provides a long lasting benefit until the next wiping event while still providing effective cleaning while providing skin barrier enhancement.

SUMMARY OF THE INVENTION

It has now been discovered that an improved wet wipe or wipe-type product, used for a variety of purposes including cleaning, cosmetics removal, and sanitation, that enhances skin barrier can be made applying, absorbing into, or otherwise wetting the wet wipe or wipe-type product with an oil-in-water emulsion composition comprising a natural fat or oil, sterol or sterol derivative, humectant, emulsifying surfactants and surfactant combinations having an HLB range of about 7 to about 18, and water. The composition also readily transfers from the wet wipe or wipe-type sheet onto the skin being contacted with the sheet to provide enhanced skin barrier benefits while providing desired product purpose.

Hence, in one aspect, the invention is an oil-in-water emulsion composition comprising from about 0.1 to about 30 weight percent of natural fats or oils, from about 0.1 to about 10 weight percent of a sterol or sterol derivative, from about 0.1 to about 99.5 weight percent of an humectant, and from about 0.5 to about 20 weight percent of an emulsifying surfactant having an HLB range of about 7 to about 18, from about 45 to about 99.5 weight percent of water and the pH of the emulsion adjusted to a pH of about 4 to about 7. PH adjustments of the composition can be made using any acid or base known in the art. One example of an acid is malic acid. Optionally, the composition may contain from about 0 to about 30 weight percent of petrolatum or mineral oil.

DETAILED DESCRIPTION OF THE INVENTION

The present invention relates to wet wipes or wipe-type products that have improved skin health benefits due to the oil-in-water emulsion composition. The wet wipes or wipe-type products of the present invention can be used for baby wipes, adult wipes, hand wipes, face wipes, cosmetic wipes, household wipes, industrial wipes, personal cleansing wipe, cotton balls, and cotton tipped swabs and the like.

One embodiment of the present invention is a wet wipe or wipe-type product that enhances skin barrier having at least one layer and an oil-in-water emulsion composition. The oil-in-water emulsion composition may comprise from about 0.1 to about 30 weight percent of natural fats or oils, from about 0.1 to about 10 weight percent of sterol or sterol derivative, from about 0.1 to about 30 weight percent of humectant, from about 0.5 to about 20 weight percent of emulsifying surfactant having an HLB range from about 7 to about 18, and from about 45 to about 99.5 weight percent of water. The emulsion composition may have a pH ranging from about 4 to about 7. PH adjustments can be made using malic acid. The amount of the oil-in-water emulsion composition contained within each wet wipe or wipe-type product may range from about 150 to about 600 weight percent based on the weight of the product.

The water contained in the composition may be a mixture of water and alcohol. The preferred alcohols are ethanol and isopropyl alcohol. The amount of alcohol in the water is up to about 70 weight percent of the water and alcohol solution. More preferably, the amount of alcohol in the water is from about 40 to about 60 weight percent of the water and alcohol solution.

The natural fat or oil used in the composition may include borage oil, avocado oil, or sunflower oil. The sterol or sterol derivative used in the composition may include soy sterol, avocado sterols, or cholesterol. The humectant used in the composition may include glycerin, sorbitol, or propylene glycol. The emulsifying surfactant used in the composition may include glyceryl stearate SE, emulsifying wax NF, or propylene glycol oleate SE. The composition may further comprise from about 0.1 to about 30 weight percent petrolatum or mineral oil.

Another embodiment of the present invention is a method of making a wet wipe or wipe-type product comprising: (a) providing at least a single layer web of nonwoven material; (b) applying an oil-in-water emulsion composition comprising a natural fat or oil, a sterol or sterol derivative, a humectant, and an emulsifying surfactant having an HLB range from about 7 to about 18, to the nonwoven material; (c) cutting said web into individual sheets to provide wet wipe or wipe-type products. In some instances, the oil-in-water emulsion composition is absorbed into said product.

Another embodiment of the present invention is a nonwoven wipe-type product that enhances skin barrier having an oil-in-water emulsion composition. The oil-in-water composition may comprise from about 0.1 to about 30 weight percent of natural fats or oils, from about 0.1 to about 10 weight percent of sterol or sterol derivative, from about 0.1 to about 30 weight percent of humectant, from about 0.5 to about 20 weight percent of emulsifying surfactant having an HLB range from about 7 to about 18, and from about 45 to about 99.5 weight percent of water. The composition may have a pH ranging from about 4 to about 7. PH adjustments can be made using malic acid.

The water contained in the composition may be a mixture of water and alcohol. The preferred alcohols are ethanol and isopropyl alcohol. The amount of alcohol in the water is up to about 70 weight percent of the water and alcohol solution. More preferably, the amount of alcohol in the water is from about 40 to about 60 weight percent of the water and alcohol solution.

Another embodiment of the present invention is a method of making a nonwoven wipe-type product comprising: (a) providing a web of nonwoven material; (b) applying an oil-in-water emulsion composition comprising a natural fat or oil, a sterol or sterol derivative, a humectant, and an emulsifying surfactant having an HLB range from about 7 to about 18, to the nonwoven material; (c) cutting said web into individual product-sized pieces wipe-type products or components for wipe-type products. In some instances, the oil-in-water emulsion composition is absorbed into said product.

Another embodiment of the present invention is an oil-in-water emulsion composition comprising from about 0.1 to about 30 weight percent of natural fats or oils, from about 0.1 to about 10 weight percent of sterol or sterol derivative, from about 0.1 to about 30 weight percent of humectant, from about 0.5 to about 20 weight percent of emulsifying surfactant having an HLB range from about 7 to about 18, and from about 45 to about 99.5 weight percent of water. The emulsion composition may also include from about 0 to about 30 weight percent of petrolatum or mineral oil. The emulsion composition may have a pH ranging from about 4 to about 7. PH adjustments can be made using malic acid.

The water contained in the composition may be a mixture of water and alcohol. The preferred alcohols are ethanol and isopropyl alcohol. The amount of alcohol in the water is up to about 70 weight percent of the water and alcohol solution.

More preferably, the amount of alcohol in the water is from about 40 to about 60 weight percent of the water and alcohol solution.

The natural fats or oils of the oil-in-water emulsion composition may be selected from the group consisting of: avocado oil, apricot oil, babassu oil, borage oil, camellia oil, canola oil, castor oil, coconut oil, corn oil cottonseed oil, evening primrose oil, hydrogenated cottonseed oil, hydrogenated palm kernel oil, maleated soybean oil, meadowfoam oil, palm kernel oil, phospholipids, rapeseed oil, palmitic acid, stearic acid, linoleic acid, stearyl alcohol, lauryl alcohol, myristyl alcohol, benenyl alcohol, rose hip oil, sunflower oil, soybean oil, and mixtures thereof. The amount of said fats or oils used in the composition may be from about 0.5 to about 10 weight percent, and more preferably from about 1 to about 5 percent.

The sterol or sterol derivatives of the oil-in-water emulsion composition may be selected from the group consisting of: cholesterol, sitosterol, stigmasterol, ergosterol, lanasterol, soy sterol, avocado sterols, cholesterol esters, sterol esters, avocadin, lanolin, and mixtures thereof.

The amount of an emulsifying surfactants used in the oil-in-water emulsion composition may be more preferably from about 1 to about 15 weight percent. The amount of the humectant used in the emulsion composition may be more preferably from about 0.5 to about 20 weight percent.

One embodiment of the composition comprises about 1 weight percent borage oil, about 0.8 weight percent soy sterol, about 5 weight percent glycerin, about 3 weight percent glyceryl stearate SE, and about 90.2 weight percent water. The emulsion composition may have a pH of about 5.5.

Another embodiment of the composition comprises about 1 weight percent borage oil, about 0.8 weight percent soy sterol, about 5 weight percent glycerin, about 3 weight percent glyceryl stearate SE, about 1 weight percent petrolatum USP, about 1 weight percent PROLIPID 141, and about 88.9 weight percent water. The emulsion composition may have a pH of about 5.5. (PROLIPID is commercially available from International Specialty Products located in Wayne, N.J. PROLIPID is generally described in U.S. Pat. No. 5,849,315 to Rerek et al. which issued Dec. 15, 1998; which is herein incorporated by reference to the extent it is consistent herewith.)

Another embodiment of the composition comprises about 0.5 weight percent Avocadin, about 0.5 weight percent sterol esters, about 5 weight percent glycerin, about 1 weight percent glyceryl stearate in the form of PROLIPID 141, and about 92 weight percent water. The emulsion composition may have a pH of about 5.5.

Another embodiment of the composition comprises about 10 weight percent sunflower oil, about 1 weight percent cholesterol, about 3 weight percent glycerin, about 5 weight percent emulsifying wax NF, and about 81 weight percent water. The emulsion composition may have a pH of about 5.5.

Another embodiment of the composition comprises about 5 weight percent avocado oil, about 1 weight percent lanasterol, about 1 weight percent sorbitol, about 5 weight percent propylene glycol oleate SE, and about 88 weight percent water. The emulsion composition may have a pH of about 5.5.

Another embodiment of the composition comprises about 10 weight percent palm kernel oil, about 1 weight percent lanasterol, about 15 weight percent hydrogenated starch hydrolysate, about 15 weight percent glyceryl stearate, about 5 weight percent petrolatum or mineral oil, and about 54 weight percent water. The emulsion composition may have a pH of about 5.5.

Another embodiment of the composition comprises about 10 weight percent lanolin, about 5 weight percent soy sterol, about 5 weight percent glycerin, about 10 weight percent emulsifying wax NF, about 5 weight percent petrolatum or mineral oil, and about 60 weight percent water. The emulsion composition may have a pH of about 5.5.

Another embodiment of composition comprises about 15 weight percent cottonseed oil, about 15 weight percent sterol esters, about 10 weight percent propylene glycol, about 15 weight percent propylene glycol oleate SE, about 10 weight percent petrolatum or mineral oil, and about 45 weight percent water. The emulsion composition may have a pH of about 5.5.

Another embodiment of the composition comprises about 30 weight percent evening primrose oil, about 5 weight percent cholesterol, about 5 weight percent sodium PCA, about 10 weight percent propylene glycol oleate SE, and about 50 weight percent water. The emulsion composition may have a pH of about 5.5.

The amount of a natural fat or oil or a mixture of natural fats or oils in the oil-in-water emulsion composition can be from about 0.1 to about 30 weight percent, more specifically from about 0.5 to about 10 weight percent, more specifically from about 1 to about 5 weight percent. As used herein, the phrase natural fats or oils is understood to include fats, oils, essential oils, fatty acids, and mixtures thereof. As used herein, suitable natural fats or oils include, but are not limited to, the following materials classified according to CTFA designations:

Fats and Oils: Apricot Kernel Oil, Avocado Oil, Babassu Oil, Borage Seed Oil, Butter, $C_{12}$–$C_{18}$ Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$–$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$–$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, and the like, as well as mixtures thereof.

Fatty Acids: Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Fatty Alcohols: Behenyl Alcohol, $C_9$–$C_{11}$ Alcohols, $C_{12}$–$C_{13}$ Alcohols, $C_{12}$–$C_{15}$ Alcohols, $C_{12}$–$C_{16}$ Alcohols, $C_{14}$–$C_{15}$ Alcohols, Caprylic Alcohol, Cetearyl Alcohol, Cetyl Alcohol, Coconut Alcohol, Decyl Alcohol, Hydrogenated Tallow Alcohol, Lauryl Alcohol, Myristyl Alcohol, Oleyl Alcohol, Palm Alcohol, Palm Kernel Alcohol, Stearyl Alcohol, Tallow Alcohol, Tridecyl Alcohol, and the like, as well as mixtures thereof.

Essential Oils: Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tea Tree Oil, Thyme Oil, Wild Mint Oil, Yarrow Oil, Ylang Ylang Oil, and the like, as well as mixtures thereof.

The preferred natural fats or oils include, but are not limited to: avocado oil, apricot oil, babassu oil, borage oil, camellia oil, canola oil, castor oil, coconut oil, corn oil, cottonseed oil, evening primrose oil, hydrogenated cottonseed oil, hydrogenated palm kernel oil, maleated soybean oil, meadowfoam oil, palm kernel oil, phospholipids, rapeseed oil, palmitic acid, stearic acid, linoleic acid, stearyl alcohol, lauryl alcohol, myristyl alcohol, benenyl alcohol, rose hip oil, sunflower oil, soybean oil, and mixtures thereof.

The amount of a sterol or sterol derivative or mixture of sterols or sterol derivatives in the oil-in-water emulsion composition can be from about 0.1 to about 10 weight percent, more specifically from about 0.5 to about 5 weight percent, and still more specifically from about 0.8 to about 3 weight percent. As used herein, suitable sterol or sterol derivative include, but are not limited to, the following materials: β-sterols having a tail on the 17 position and having no polar groups, for example cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyidecanoate, dihydrolanosterol, dihydrolanosteryl octyldecanoate, ergocalciferol, tall oil sterol, soy sterol acetate, lanasterol, soy sterol, avocado sterols, cholesterol esters, sterol esters, avocadin, lanolin, and the like, as well as mixtures thereof.

The amount of an emulsifying surfactant having an HLB range of about 7 to about 18 in the oil-in-water emulsion composition can be from about 0.5 to about 20 weight percent, more specifically from about 1 to about 15 weight percent, and still more specifically from about 3 to about 10 weight percent. Emulsifying surfactants are employed typically in cosmetic preparations to form emulsions of various components. The immiscible phase, such as an oil, is dispersed as droplets in the continuous phase, such as water. As used herein, suitable surfactants include, but are not limited to, the following materials: Almond Oil PEG-6 Esters, Apricot Kernel Oil PEG-6 Esters, Avocado Oil PEG-11 Esters, Beheneth-5, Beheneth-10, Beheneth-20, $C_{18}$–$C_{36}$ Acid Glycol Ester, $C_{12}$–$C_{20}$ Acid PEG-8 Ester, Calcium Stearoyl Lactylate, Canola Oil Glyceride, Caprylic/Capric Triglyceride PEG-4 Esters, Beheneth-5, Beheneth-10, Beheneth-20, Cetearyl Glucoside, Ceteth-1, Ceteth-2, Ceteth-3, Ceteth-4, Ceteth-5, Ceteth-6, Ceteth-10, Ceteth-12, Ceteth-15, Ceteth-16, Cetyl Phosphate, Choleth-10, Choleth-20, Choleth-24, Coceth-3, Coceth-5, Coceth-8, Coceth-10, Corn Glycerides, Corn Oil PEG-6 Esters, Corn Oil PEG-8 Esters, Cottonseed Glyceride, $C_9$–$C_{11}$ Pareth-3, $C_9$–$C_{11}$ Pareth-6, $C_9$–$C_{11}$ Pareth-8, $C_{11}$–$C_{15}$ Pareth-3, $C_{11}$–$C_{15}$ Pareth-5, $C_{11}$–$C_{15}$ Pareth-7, $C_{11}$–$C_{15}$ Pareth-9, $C_{11}$–$C_{15}$ Pareth-12, $C_{11}$–$C_{15}$ Pareth-15, $C_{11}$–$C_{15}$ Pareth-20, $C_{11}$–$C_{21}$ Pareth-3, $C_{11}$–$C_{21}$ Pareth-10, $C_{12}$–$C_{13}$ Pareth-3, $C_{12}$–$C_{13}$ Pareth-7, $C_{12}$–$C_{13}$ Pareth-9, $C_{12}$–$C_{13}$ Pareth-15, $C_{12}$–$C_{15}$ Pareth-2, $C_{12}$–$C_{15}$ Pareth-3, $C_{12}$–$C_{15}$ Pareth-4, $C_{12}$–$C_{15}$ Pareth-5, $C_{12}$–$C_{15}$ Pareth-7, $C_{12}$–$C_{15}$ Pareth-9, $C_{12}$–$C_{15}$ Pareth-11, $C_{12}$–$C_{15}$ Pareth-12, $C_{14}$–$C_{15}$ Pareth-12, $C_{14}$–$C_{15}$ Pareth-7, $C_{14}$–$C_{15}$ Pareth-11, $C_{14}$–$C_{15}$ Pareth-13, $C_{20}$–$C_{40}$ Pareth-3, $C_{20}$–$C_{40}$ Pareth-10, $C_{30}$–$C_{50}$ Pareth-3, $C_{30}$–$C_{50}$ Pareth-10, $C_{40}$–$C_{60}$ Pareth-3, $C_{40}$–$C_{60}$ Pareth-10, $C_{12}$–$C_{15}$ Pareth-2 Phosphate, DEA-Cetyl Phosphate, DEA-Oleth-3 Phosphate, DEA-Oleth-10 Phosphate, Deceth-4, Deceth-6, Deceth4 Phosphate, Deceth-6 Phosphate, Dextrin Palmitate, Diceteareth-10 Phosphate, Dicetyl Phosphate, Diethylaminoethyl Cocoate, Diethylaminoethyl PEG-5 Cocoate, Diethylaminoethyl PEG-5 Laurate, Diethylaminoethyl Stearate, Diglyceryl Caprylate, Dihydrocholeth-15, Dihydrocholeth-20, Dihydrocholeth-30, Dialaureth-4 Phosphate, Dilaureth-10 Phosphate, Dimethicone Copolyol Methyl Ether, Dimethyl Octynediol, Dinonoxynol-9 Citrate, Dinonoxynol-4 Phosphate, Dioleth-8 Phosphate, Disodium Lauryl Phosphate, Disodium PEG-8 Glyceryl Caprylate/Caprate, Dodoxynol-5, Dodoxynol-6, Dodoxynol-7, Dodoxynol-9, Dodoxynol-12, Emulsifying wax NF, Glycereth-20 Stearate, Glyceryl Behenate, Glyceryl Caprate, Glyceryl Caprylate, Glyceryl Caprylate/Caprate, Glyceryl Cocoate, Glyceryl Erucate, Glyceryl Hydrogenated Rosinate, Glyceryl Hydroxystearate, Glyceryl Isostearate, Glyceryl Lanolate, Glyceryl Laurate, Glyceryl Laurate/Oleate, Glyceryl Laurate SE, Glyceryl Linoleate, Glyceryl Linolenate, Glyceryl Montanate, Glyceryl Myristate, Glyceryl Oleate, Glyceryl Oleate SE, Glyceryl Palmitate/Stearate, Glyceryl Ricinoleate, Glyceryl Rosinate, Glyceryl/Sorbitol Oleate/Hydroxystearate, Glyceryl Stearate, Glyceryl Stearate SE, Glycol Stearate SE, Hydrogenated Cottonseed Glyceride, Hydrogenated Laneth-5, Hydrogenated Laneth-20, Hydrogenated Lard Glyceride, Hydrogenated Lecithin, Hydrogenated Palm Glyceride, Hydrogenated Palm/Palm Kernel Oil PEG-6 Esters, Hydrogenated Soy Glyceride, Hydrogenated Talloweth-12, Hydrogenated Talloweth-60 Myristyl Glycol, Hydrogenated Tallow Glyceride, Hydrogenated Vegetable Glyceride, Hydrogenated Vegetable Glycerides Phosphate, Hydroxycetyl Phosphate, Hydroxylated Lecithin, Isoceteareth-8 Stearate, Isoceteth-10, Isoceteth-20, Isoceteth-10 Stearate, Isodeceth4, Isodeceth-5, Isodeceth-6, Isolaureth-3, Isolaureth-6, Isolaureth-10, Isosteareth-2, Isosteareth-3, Isosteareth-10, Isosteareth-12, Isosteareth-20, Isosteareth-6 Carboxylic Acid, Isosteareth-11 Carboxylic Acid, Isosteareth-10 Stearate, Laneth-5, Laneth-10, Laneth-15, Laneth-16, Laneth-4 Phosphate, Lanolin, Laureth-1, Laureth-2, Laureth-3, Laureth-4, Laureth-5, Laureth-6, Laureth-7, Laureth-8, Laureth-9, Laureth-10, Laureth-11, Laureth-12, Laureth-13, Laureth-14, Laureth-15, Laureth-16, Laureth-3 Carboxylic Acid, Lauryl Phosphate, Lecithin, Mannitan Laurate, Meroxapol 105, Meroxapol 108, Meroxapol 174, Meroxapol 251, Meroxapol 252, Meroxapol 311, Meroxapol 312, Mink Oil PEG-13 Esters, Myreth-3, Myreth-4, Myreth-5, Myreth-10, Noneth-8, Nonoxynol-1, Nonoxynol-2, Nonoxynol-3, Nonoxynol-4, Nonoxynol-5, Nonoxynol-6, Nonoxynol-7, Nonoxynol-8, Nonoxynol-9, Nonoxynol-10, Nonoxynol-11, Nonoxynol-12, Nonoxynol-13, Nonoxynol-14, Nonoxynol-15, Nonoxynol-18, Nonoxynol-20, Nonoxynol-6 Phosphate, Nonoxynol-9 Phosphate, Nonoxynol-10 Phosphate, Nonyl Nonoxynol-5, Nonyl Nonoxynol-10, Nonyl Nonoxynol-7 Phosphate, Nonyl Nonoxynol-9 Phosphate, Nonyl Nonoxynol-10 Phosphate, Octoxyglyceryl Behenate, Octoxyglyceryl Palmitate, Octoxynol-1, Octoxynol-3, Octoxynol-5, Octoxynol-7, Octoxynol-8, Octoxynol-9, Octoxynol-10, Octoxynol-11, Octoxynol-12, Octoxynol-13, Octoxynol-16, Octoxynol-20, Octoxynol-9 Carboxylic Acid, Octyldodeceth-16, Octyldodeceth-20, Oleth-2, Oleth-3, Oleth-4, Oleth-5, Oleth-6, Oleth-7, Oleth-8, Oleth-9, Oleth-10, Oleth-12, Oleth-15, Oleth-16, Oleth-20, Oleth-2 Phosphate, Oleth-3 Phosphate, Oleth-4 Phosphate, Oleth-10 Phosphate, Oleth-20 Phosphate, Olive Oil PEG-6 Esters, Olive Oil PEG-10 Esters, Palm Glyceride, Peanut Oil PEG-6 Esters, PEG-20 Almond Glycerides, PEG-60 Almond Glycerides, PEG-11 Avocado Glycerides PEG-6 Beeswax, PEG-8 Beeswax, PEG-8 Behenate, PEG-8 Caprate, PEG-8 Caprylate, PEG-8 Caprylate/Caprate, PEG-6 Caprylic/Capric Glycerides, PEG-8 Caprylic/Capric Glycerides, PEG-2 Castor Oil, PEG-3 Castor Oil, PEG-4 Castor Oil, PEG-5 Castor Oil, PEG-8 Castor Oil, PEG-9 Castor Oil, PEG-10 Castor Oil, PEG-11 Castor Oil, PEG-15 Castor Oil, PEG-20 Castor Oil, PEG-25 Castor Oil, PEG-30 Castor Oil, PEG-33 Castor Oil, PEG-35 Castor Oil, PEG-36 Castor Oil, PEG-8 $C_{12}$–$C_{18}$ Ester, PEG-3 Cocamide, PEG-5 Cocamide, PEG-6 Cocamide, PEG-7 Cocamide, PEG-11 Cocamide, PEG-2 Cocamine, PEG-3 Cocamine, PEG-5 Cocamine, PEG-10 Cocamine, PEG-15 Cocamine, PEG-20 Cocamine, PEG-15 Cocamine Oleate/Phosphate, PEG-75 Cocoa Butter Glycerides, PEG-5 Cocoate, PEG-8 Cocoate, PEG-15 Cocoate, PEG-10 Coconut Oil Esters, PEG-15 Cocopolyamine, PEG-20 Corn Glycerides, PEG-60 Corn Glycerides, PEG-8 Dicocoate, PEG-2 Diisononanoate, PEG-8 Diisostearate, PEG-2 Dilaurate, PEG-4 Dilaurate, PEG-6 Dilaurate, PEG-8 Dilaurate, PEG-12 Dilaurate, PEG-20 Dilaurate, PEG-32 Dilaurate, Peg-2 Dioctanoate, PEG-4 Dioleate, PEG-6 Dioleate, PEG-8 Dioleate, PEG-10 Dioleate, PEG-12 Dioleate, PEG-20 Dioleate, PEG-32 Dioleate, PEG-3 Dipalmitate, PEG-13 Diphenylol Propane, PEG-2 Distearate, PEG-3 Distearate, PEG-4 Distearate, PEG-6 Distearate, PEG-8 Distearate, PEG-9 Distearate, PEG-12 Distearate, PEG-20 Distearate, PEG-32 Distearate, PEG-8 Ditallate, PEG-12 Ditallate, PEG-8 Di/Triricinoleate, PEG-60 Evening Primrose Glycerides, PEG-7 Glyceryl Cocoate, PEG-12 Glyceryl Dioleate, PEG-15 Glyceryl Isostearate, PEG-20 Glyceryl isostearate, PEG-12 Glyceryl Laurate, PEG-20 Glyceryl Laurate, PEG-10 Glyceryl Oleate, PEG-15 Glyceryl Oleate, PEG-20 Glyceryl Oleate, PEG-15 Glyceryl Ricinoleate, PEG-20 Glyceryl Ricinoleate, PEG-5 Glyceryl Sisquioleate, PEG-5 Glyceryl Stearate, PEG-10 Glyceryl Stearate, PEG-5 Glyceryl Triisostearate, PEG-25 Glyceryl Trioleate, PEG-5 Hydrogenated Castor Oil, PEG-16 Hydrogenated Castor Oil, PEG-20 Hydrogenated Castor Oil, PEG-25 Hydrogenated Castor Oil, PEG-30 Hydrogenated Castor Oil, PEG-35 Hydrogenated Castor Oil, PEG-40 Hydrogenated Castor Oil, PEG-5 Hydrogentated Corn Glycerides, PEG-8 Fish Glycerides, PEG-5 Hydrogenated Lanolin, PEG-10 Hydrogenated Lanolin, PEG-20 Hydrogenated Lanolin, PEG-24 Hydrogenated Lanolin, PEG-20 Hydrogenated Palm Oil Glycerides, PEG-13 Hydrogenated Tallow Amide, PEG-8 Hydrogenated Tallow Amine, PEG-10 Hydrogenated Tallow Amine, PEG-15 Hydrogenated Tallow Amine, PEG-20 Hydrogenated Tallow Amine, PEG-15 Hydroxystearate, PEG-6 Isolauryl Thioether, PEG-8 Isolauryl Thioether, PEG-10 Isolauryl Thioether, PEG-6 Isopalmitate, PEG-4 Isostearate, PEG-6 Isostearate, PEG-8 Isostearate, PEG-10 Isostearate, PEG-12 Isostearate, PEG-15 Jojoba Acid, PEG-26 Jojoba Acid, PEG-40 Jojoba Acid, PEG-15 Jojoba Alcohol, PEG-26 Jojoba Alcohol, PEG-5 Lanolate, PEG-10 Lanolate, PEG-20 Lanolate, PEG-5 Lanolin, PEG-10 Lanolin, PEG-20 Lanolin, PEG-24 Lanolin, PEG-27 Lanolin, PEG-30 Lanolin, PEG-40 Lanolin, PEG-75 Lanolin Wax, PEG-3 Lauramide, PEG-5 Lauramide, PEG-6 Lauramide, PEG-2 Laurate, PEG-4 Laurate, PEG-6 Laurate, PEG-8 Laurate, PEG-9 Laurate, PEG-10 Laurate, PEG-12 Laurate, PEG-14 Laurate, PEG-2 Laurate SE, PEG-6 Laurate/Tartarate, PEG-8 Linoleate, PEG-8 Linolenate, PEG-20 Methyl Glucose Distearate, PEG-20 Methyl Glucose Sesquicaprylate/Sesquicaprate, PEG-20 Methyl Glucose Sesquilaurate, PEG-20 Methyl Glucose Sesquistearate, PEG-13 Mink Glycerides, PEG-8 Myristate, PEG-20 Myristate, PEG-4 Octanoate, PEG-5 Octanoate, PEG-13 Octanoate, PEG-2 Oleamide, PEG-4 Oleamide, PEG-5 Oleamide, PEG-6 Oleamide, PEG-7 Oleamide, PEG-9 Oleamide, PEG-2 Oleamine, PEG-5 Oleamine, PEG-15 Oleamine, PEG-2 Oleate, PEG-3 Oleate, PEG4 Oleate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-14 Oleate, PEG-15 Oleate, PEG-20 Oleate, PEG-2 Oleate SE, PEG-10 Olive Glycerides, PEG-6 Palmitate, PEG-18 Palmitate, PEG-20 Palmitate, PEG-12 Palm Kernel Glycerides, PEG-45 Palm Kernel Glycerides, PEG-25 Phytosterol, PEG-10 Polyglyceryl-2 Laurate, PEG-3/PPG-2 Glyceryl/Sorbitol Hydroxystearate/Isostearate, PEG-20-PPG-10 Glyceryl Stearate, PEG4 Proline Linoleate, PEG-4 Proline Linolenate, PEG-8 Propylene Glycol Cocoate, PEG-4 Rapeseedamide, PEG-2 Ricinoleate, PEG-7 Ricinoleate, PEG-8 Ricinoleate, PEG-9 Ricinoleate, PEG-8 Sesquilaurate, PEG-8 Sesquioleate, PEG-6 Sorbitan Beeswax, PEG-8 Sorbitan Beeswax, PEG-20 Sorbitan Beeswax, PEG-40 Sorbitan Diisostearate, PEG-5 Sorbitan Isostearate, PEG-20 Sorbitan Isostearate, PEG-3 Sorbitan Oleate, PEG-6 Sorbitan Oleate, PEG-40 Sorbitan Peroleate, PEG-3 Sorbitan Stearate, PEG-6 Sorbitan Stearate, PEG-30 Sorbitan Tetraoleate, PEG-40 Sorbitan Tetraoleate, PEG-60 Sorbitan Tetraoleate, PEG-60 Sorbitan Tetrastearate, PEG-40 Sorbitol Hexaoleate, PEG-50 Sorbitol Hexaoleate, PEG-30 Sorbitol Tetraoleate Laurate, PEG-5 Soyamine, PEG-8 Soyamine, PEG-10 Soyamine, PEG-15 Soyamine, PEG-5

Soya Sterol, PEG-10 Soya Sterol, PEG-16 Soya Sterol, PEG-25 Soya Sterol, PEG-4 Stearamide, PEG-5 Stearamine, PEG-10 Stearamine, PEG-15 Stearamine, PEG-2 Stearate, PEG-3 Stearate, PEG-4 Stearate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-18 Stearate, PEG-20 Stearate, PEG-2 Stearate SE, PEG-4 Tallate, PEG-5 Tallate, PEG-8 Tallate, PEG-10 Tallate, PEG-12 Tallate, PEG-16 Tallate, PEG-20 Tallate, PEG-5 Tallow Amide, PEG-8 Tallow Amide, PEG-20 Tallowate, PEG-5 Tricaprylyl Citrate, PEG-5 Tricetyl Citrate, PEG-5 Tridecyl Citrate, PEG-5 Trilauryl Citrate, PEG-5 Trimyristyl Citrate, PEG-5 Tristearyl Citrate, PEG-6 Undecylenate, Pelargonic Acid, Poloxamer 101, Poloxamer 105, Poloxamer 122, Poloxamer 123, Poloxamer 124, Poloxamer 181, Poloxamer 185, Poloxamer 212, Poloxamer 215, Poloxamer 231, Poloxamer 282, Poloxamer 284, Poloxamer 331, Poloxamer 333, Poloxamer 401, Poloxamer 402, Poloxamer 403, Poloxamer 407, Poloxamine 304, Poloxamine 304, Poloxamine 504, Poloxamine 701, Poloxamine 702, Poloxamine 704, Poloxamine 707, Poloxamine 901, Poloxamine 904, Poloxamine 1101, Poloxamine 1102, Poloxamine 1104, Poloxamine 1301, Poloxamine 1302, Poloxamine 1304, Poloxamine 1307, Poloxamine 1501, Poloxamine 1502, Poloxamine 1504, Polyglyceryl-3 Beeswax, Polyglyceryl-3 Cetyl Ether, Polyglyceryl-4 Cocoate, Polyglyceryl-10 Decalinoleate, Polyglyceryl-10 Decaoleate, Polyglyceryl-10 Decastea rate, Polyglyceryl-3 Decyltetradecanol, Polyglyceryl-2 Diisostearate, Polyglyceryl-3 Diisostearate, Polyglyceryl-10 Diisostearate, Polyglyceryl-2 Dioleate, Polyglyceryl-3 Dioleate, Polyglyceryl-6 Dioleate, Polyglyceryl-10 Dioleate, Polyglyceryl-3 Distearate, Polyglyceryl-6 Distearate, Polyglyceryl-10 Distearate, Polyglyceryl-10 Heptaoleate, Polyglyceryl-10 Heptastearate, Polyglyceryl-6 Hexaoleate, Polyglyceryl-3 Hydroxylauryl Ether, Polyglyceryl-2 Isostearate, Polyglyceryl-4 Isostearate, Polyglyceryl-6 Isostearate, Polyglyceryl-2 Lanolin Alcohol Ether, Polyglyceryl-10 Laurate, Polyglyceryl-4 Lauryl Ether, Polyglyceryl-10 Myristate, Polyglyceryl-2 Oleate, Polyglyceryl-3 Oleate, Polyglyceryl-4 Oleate, Polyglyceryl-6 Oleate, Polyglyceryl-8 Oleate, Polyglyceryl-10 Oleate, Polyglyceryl-2 Oleyl Ether, Polyglyceryl-4 Oleyl Ether, Polyglyceryl-4-PEG-2 Cocamide, Polyglyceryl-2-PEG-4 Stearate, Polyglyceryl-6 Pentaoleate, Polyglyceryl-10 Pentaoleate, Polyglyceryl-6 Pentastearate, Polyglyceryl-10 Pentastearate, Polyglyceryl-2 Sesquilsostearate, Polyglyceryl-2 Sesquioleate, Polyglyceryl-2 Stearate, Polyglyceryl-3 Stearate, Polyglyceryl-4 Stearate, Polyglyceryl-8 Stearate, Polyglyceryl-10 Stearate, Polyglyceryl-3 Stea rate SE, Polyglyceryl-2 Tetraisostearate, Polyglyceryl-10 Tetraoleate, Polyglyceryl-2 Tetrastearate, Polyglyceryl-2 Triisostearate, Polyglyceryl-10 Trioleate, Polyglyceryl-6 Tristearate, Polysorbate 20, Polysorbate 21, Polysorbate 40, Polysorbate 60, Polysorbate 61, Polysorbate 65, Polysorbate 80, Polysorbate 81, Polysorbate 85, Polysorbate 80 Acetate, Potassium Castorate, Potassium Cetyl Phosphate, Potassium Cocoate, Potassium Cornate, Potassium Laurate, Potassium Myristate, Potassium Octoxynol-12 Phosphate, Potassium Oleate, Potassium Palmitate, Potassium Ricinoleate, Potassium Stearate, Potassium Tallate, Potassium Tallowate, PPG-7-Buteth-10, PPG-9-Buteth-12, PPG-12-Buteth-16, PPG-15-Buteth-20, PPG-20-Buteth-30, PPG-24-Buteth-27, PPG-26-Buteth-26, PPG-28-Buteth-35, PPG-25 Butyl Ether Phosphate, PPG-2-Ceteareth-9, PPG-4-Ceteareth-12, PPG-10-Ceteareth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-5-Ceteth-10 Phosphate, PPG-10 Cetyl Ether Phosphate, PPG-6 $C_{12}$–$C_{18}$ Pareth-11, PPG-2-Deceth-10, PPG-4-Deceth-4, PPG-6-Deceth-4, PPG-6-Deceth-9, PPG-8-Deceth-6, PPG-6-Decyltetradeceth-12, PPG-6-Decyltetradeceth-20, PPG-6-Decyltetradeceth-30, PPG-20-Decyltetradeceth-10, PPG-24-Glycereth-24, PPG-66-Glycereth-12, PPG-10 Glyceryl Ether, PPG-27 Glyceryl Ether, PPG-55 Glyceryl Ether, PPG-2 Isoceteth-20 Acetate, PPG-2-Isodeceth4, PPG-2-Isodeceth-6, PPG-2-Isodeceth-9, PPG-2-Isodeceth-12, PPG-3-Isosteareth-9, PPG4 Jojoba Acid, PPG-4 Jojoba Alcohol, PPG-10 Jojoba Alcohol, PPG-12-Laneth-50, PPG-3-Laureth-9, PPG-4-Laureth-2, PPG-4-Laureth-5, PPG-4-Laureth-7, PPG-5-Laureth-5, PPG-25-Laureth-25, PPG-7 Lauryl Ether, PPG-3-Myreth-3, PPG-3-Myreth-11, PPG-2-PEG-6 Coconut Oil Ethers, PPG-12-PEG-50 Lanolin, PPG-12-PEG-65 Lanolin Oil, PPG-40-PEG-60 Lanolin Oil, PPG-8 Polyglyceryl-2 Ether, Propylene Glycol Capreth-4, Propylene Glycol Caprylate, Propylene Glycol Hydroxystearate, Propylene Glycol Isodeceth-4, Propylene Glycol Isodeceth-12, Propylene Glycol Isostearate, Propylene Glycol Laurate, Propylene Glycol Linoleate, Propylene Glycol Linolenate, Propylene Glycol Myristate, Propylene Glycol Oleate, Propylene Glycol Oleate SE, Propylene Glycol Oleth-5, Propylene Glycol Ricinoleate, Propylene Glycol Soyate, Propylene Glycol Stearate, Propylene Glycol Stearate SE, Raffinose Oleate, Safflower Glyceride, Sodium Caproyl Lactylate, Sodium Caprylate, Sodium Capryleth-9 Carboxylate, Sodium Castorate, Sodium Ceteth-13 Carboxylate, Sodium Coceth Sulfate, Sodium Cocoate, Sodium Coco/Hydrogenated Tallow Sulfate, Sodium Diceteareth-10 Phosphate, Sodium Isostearoyl Lactylate, Sodium Laurate, Sodium Laureth-4 Phosphate, Sodium Lauroyl Lactylate, Sodium/MEA Laureth-2 Sulfosuccinate, Sodium Myristate, Sodium Oleate, Sodium Oleoyl Lactylate, Sodium Oleth-7 Phosphate, Sodium Oleth-8 Phosphate, Sodium Palmitate, Sodium Palm Kernelate, Sodium Ricinoleate, Sodium Stearate, Sodium Steareth-4 Phosphate, Sodium Stearoyl Lactylate, Sodium Stearyl Sulfate, Sodium Trideceth Sulfate, Sodium Tridecyl Sulfate, Sodium Undecylenate, Sorbeth-6 Hexastearate, Sorbitan Diisostearate, Sorbitan Dioleate, Sorbitan Distearate, Sorbitan Isostearate, Sorbitan Laurate, Sorbitan Oleate, Sorbitan Palmitate, Sorbitan Sesquiisostearate, Sorbitan Sesquioleate, Sorbitan Sesquistearate, Sorbitan Stearate, Sorbitan Triisostearate, Sorbitan Trioleate, Sorbitan Tristearate, Soy Acid, Steareth-2, Steareth-3, Steareth-4, Steareth-5, Steareth-6, Steareth-7, Steareth-10, Steareth-11, Steareth-13, Steareth-15, Steareth-16, Steareth-20, Steareth-21, Stearic Acid, Stearoyl Lactylic Acid, Sucrose Cocoate, Sucrose Kilaurate, Sucrose Distearate, Sucrose Laurate, Sucrose Myristate, Sucrose Oleate, Sucrose Palmitate, Sucrose Polylaurate, Sucrose Polylinoleate, Sucrose Polyoleate, Sucrose Polystearate, Sucrose Ricinoleate, Sucrose Stearate, Sunflower Seed Oil Glyceride, Tall Oil Acid, Gallow Acid, Talloweth-6, Tallow Glyceride, TEA-Isostearate, TEA-Lauroyl Lactylate, TEA-Myristate, TEA-Oleate, TEA-Palmitate, TEA-Stearate, TEA-Tallate, TIPA-Stearate, Triceteareth-4 Phosphate, Triceteth-5 Phosphate, Trideceth-2, Trideceth-3, Trideceth-6, Trideceth-7, Trideceth-9, Trideceth-10, Trideceth-11, Trideceth-12, Trideceth-15, Trideceth-20, Trideceth-3 Phosphate, Trideceth-6 Phosphate, Triisostearin PEG-6 Esters, Trilaneth-4 Phosphate, Trilaureth-4 Phosphate, Triolein PEG-6 Esters, Trioleth-8 Phosphate, Undecanoic Acid, Undeceth-5, Undecyleneth-6, Vegetable Glycerides Phosphate, and the like, as well as mixtures thereof.

The preferred surfactants include, but are not limited to: emulsifying wax NF, glyceryl stearate, glyceryl stearate SE glycol stearate, glycol stearate SE, glycereth-20 Stearate, glyceryl behenate, glyceryl hydroxystearate, glyceryl laurate SE, glycerly oleate, glyceryl oleate SE, propylene glycol oleate, propylene glycol oleate SE, propylene glycol stearate, propylene glycol stearate SE, sorbitan stearate, sorbitan trioleate, and the like, as well as mixtures thereof.

The amount of humectant in the oil-in-water emulsion composition can be from is about 0.1 to about 30 weight percent, more specifically from about 0.5 to about 20 weight percent, and still more specifically from about 1 to about 10 weight percent. Humectants are typically cosmetic ingredients used to increase the water content of the top layers of the skin. This group of materials includes primarily hydroscopic ingredients. As used herein, suitable humectants include, but are not limited to, the following materials: Acetamide MEA, Aloe Vera Gel, Arginine PCA, Chitosan PCA, Copper PCA, Corn Glycerides, Dimethyl Imidazolidinone, Fructose, Glucamine, Glucose, Glucose Glutamate, Glucuronic Acid, Glutamic Acid, Glycereth-7, Glycereth-12, Glycereth-20, Glycereth-26, Glycerin, Honey, Hydrogenated Honey, Hydrogenated Starch Hydrolysate, Hydrolyzed Corn Starch, Lactamide MEA, Lactic Acid, Lactose Lysine PCA, Mannitol, Methyl Gluceth-10, Methyl Gluceth-20, PCA, PEG-2 Lactamide, PEG-10 Propylene Glycol, Polyamino Sugar Condensate, Potassium PCA, Propylene Glycol, Propylene Glycol Citrate, Saccharide Hydrolysate, Saccharide Isomerate, Sodium Aspartate, Socium Lactate, Sodium PCA, Sorbitol, TEA-Lactate, TEA-PCA, Urea, Xylitol, and the like, as well as mixtures thereof.

The amount of water in the oil-in-water emulsion composition can be from about 45 to about 99.5 weight percent, more specifically from about 60 to about 98 weight percent, and still more specifically from about 75 to about 95 weight percent.

The amount of petrolatum or mineral oil that can optionally be used in the oil-in-water composition can be from about 0 to about 30 weight percent, more specifically from about 0 to about 10 weight percent, and still more specifically from about 0 to about 5 weight percent.

The pH should be adjusted the approximate pH of the skin with a suitable acid or base. The pH of the composition can be about 4.0 to about 7.0, more specifically from about 5.0 to about 6.0 and more specifically from about 5.4 to about 5.6. In some product lines, such as certain facial wipes, it may be desirable to have a pH range from about 2 to about 8.

In order to better enhance the benefits to consumers, additional ingredients can be used. The classes of ingredients and their corresponding benefits include, without limitation: antiacne actives (a drug product used to reduce the number of acne blemishes, acne pimples, blackheads, and whiteheads); antifoaming agents (reduce the tendency of foaming during processing); antimicrobial actives; antifungal actives; antiseptic actives; antioxidants (product integrity); antioxidants (to prevent oxidation of the natural oils and other ingredients in the formulation); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product including vitamins); colorants (impart color to the product); deodorants (reduce or eliminate unpleasant odor and protect against the formation of malodor on body surfaces); emollients (help to maintain the soft, smooth, and pliable appearance of the skin by their ability to remain on the skin surface or in the stratum corneum to act as lubricants, to reduce flaking, and to improve the skin's appearance); film formers (to hold active ingredients on the skin by producing a continuous film on skin upon drying); fragrances (consumer appeal); natural moisturizing agents (NMF) and other skin moisturizing ingredients known in the art; preservatives (prevent microbial contamination and growth); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); solvents (liquids employed to dissolve components found useful in the cosmetics or drugs); sunscreens (ingredients that absorb at least 85 percent of the light in the UV range at wavelengths from 290 to 320 manometers, but transmit UV light at wavelengths longer than 320 manometers); and, surfactants (as cleansing agents, solubilizing agents, suspending agents, and wetting agents).

The wet wipes of the present invention comprise a single layer or a layered basesheet that contains a liquid. The liquid is typcially any solution which can be absorbed into the wet wipe basesheet and may include any suitable components which provide the desired wiping properties. Typically, the components have included water, emollients, surfactants, fragrances, preservatives, chelating agents, pH buffers or combinations thereof as are well known to those skilled in the art. The liquid has also contained certain lotions and/or medicaments. The emulsion composition of the present invention is more specifically designed to provide improved skin health benefits, such as enhanced barrier function and protection of the skin.

The amount of the oil-in-water emulsion composition of the present invention contained within each wet wipe may vary depending upon the type of material being used to provide the wet wipe or wipe-type product, the type of container being used to store the wet wipes, and the desired end use of the wet wipe. Generally, each wet wipe or wipe-type product can contain from about 100 to about 600 weight percent and desirably from about 250 to about 450 weight percent liquid based on the dry weight of the wipe for improved wiping. In a particular aspect, the amount of liquid contained within the wet wipe is from about 300 to about 400 weight percent and desirably about 330 weight percent based on the dry weight of the wet wipe. If the amount of liquid is less than the above-identified ranges, the wet wipe may be too dry and may not adequately perform. If the amount of liquid is greater than the above-identified ranges, the wet wipe may be oversaturated and soggy and the liquid may pool in the bottom of the container.

Each wet wipe is generally rectangular in shape and may have any suitable unfolded width and length. For example, the wet wipe may have an unfolded length of from about 2.0 to about 80.0 centimeters and desirably from about 10.0 to about 25.0 centimeters and an unfolded width of from about 2.0 to about 80.0 centimeters and desirably from about 10.0 to about 25.0 centimeters. Typically, each individual wet wipe is arranged in a folded configuration and stacked one on top of the other to provide a stack of wet wipes. Such folded configurations are well known to those skilled in the art and include c-folded, z-folded, quarter-folded configurations and the like. The stack of folded wet wipes may be placed in the interior of a container, such as a plastic tub, to provide a package of wet wipes for eventual sale to the consumer. Alternatively, the wet wipes may include a continuous strip of material which has perforations between each wipe and which may be arranged in a stack or wound into a roll for dispensing.

However, the wet wipe or wipe-type product may assume a variety of shapes, including but not limited to, generally circular, oval, square, or irregularly shaped. The size of the wet wipe or wipe-type product will also vary depending upon the desired end use of the wipe.

The materials of the basesheet, single or multi-layered, of the wet wipe or the wipe-type product of the present invention may be varied to provide different physical properties. The different physical properties which a layer may be configured to provide by selecting the appropriate materials include softness, resiliency, strength, flexibility, integrity, toughness, absorbency, liquid retention, thickness, tear resistance, surface texture, drapability, hand, wettability, wicking ability and the like and combinations thereof. The wipe can be configured to provide all desired physical properties within one layer or configured to provide only specific physical properties within individual layers of a multi-layered wipe. For example, the wet wipes may include at least one layer of material that is configured to provide strength and resilience to the wet wipe and at least one other layer which is configured to provide a soft, gentle wiping surface to the wet wipe. Desirably, the wet wipes provide a soft wiping surface for contact with the skin.

The layer or layers of the wet wipe or wipe-type products can be made from a variety of materials including meltblown materials, coform materials, air-laid materials, bonded-carded web materials, hydroentangled materials, spunbond materials and the like and can comprise synthetic or natural fibers. Examples of natural fibers suitable for use in the present invention include cellulosic fibers such as wood pulp fibers, cotton fibers, flax fibers, jute fibers, silk fibers and the like. Examples of thermoplastic polymeric fibers suitable for use with the present invention include polyolefins such as polypropylene and polyethylene, polyamides, and polyesters such as polyethylene teraphthalate. Alternative synthetic fibers which may be suitable include staple nylon and rayon fibers. The layer or layers of the wet wipe or wipe-type products can be woven or nonwoven materials. In addition, the materials can be formed into balls, such as cotton balls, or applied to delivery systems such as applicators for swabs.

If a layer of the basesheet is a combination of polymeric and natural fibers, such as polypropylene and cellulosic fibers, the relative percentages of the polymeric fibers and natural fibers in the layer can vary over a wide range depending on the desired characteristics of the wet wipes. For example, the layer may comprise from about 20 to about 95 weight percent, desirably from about 20 to about 60 weight percent, and more desirably from about 30 to about 40 weight percent of polymeric fibers based on the dry weight of the layer. Such a layer of polymeric and natural fibers may be manufactured by any method known to those skilled in the art.

Generally, it is desirable that such a layer be formed by a coform process for a more uniform distribution of the polymeric and natural fibers within the layer. Such coform layers are manufactured generally as described in U.S. Pat. No. 4,100,324 to Anderson et al. which issued Jul. 11, 1978; U.S. Pat. No. 4,604,313 to McFarland et al. which issued Aug. 5, 1986; and U.S. Pat. No. 5,350,624 which issued Sep. 27, 1994; which are herein incorporated by reference to the extent they are consistent herewith.

Typically, such coform layers comprise a gas-formed matrix of thermoplastic polymeric meltblown microfibers, such as, for example, polypropylene microfibers, and cellulosic fibers, such as, for example, wood pulp fibers. A coform layer is formed by initially forming at least one primary air stream containing the synthetic or polymeric fibers and merging the primary stream with at least one secondary stream of natural or cellulosic fibers. The primary and secondary streams are merged under turbulent conditions to form an integrated stream containing a thorough, homogeneous distribution of the different fibers. The integrated air stream is directed onto a forming surface to air form the layer of material. A multiplicity of these coform layers can then be formed in succession to provide a web of multiple coform layers.

The different fibers in the different layers of the layered basesheet of the present invention, such as the polypropylene and polyethylene microfibers set forth above, typically may not be compatible with and may not bond to each other. However, the different fibers may entangle with each other resulting in suitable securement between the layers. For example, in a layered basesheet containing a coform layer of polyethylene and cellulosic fibers and a coform layer of polypropylene and cellulosic fibers, the polyethylene and polypropylene fibers may entangle with each other and the cellulosic fibers and may at least partially bond to the cellulosic fibers which results in securement between the layers.

Such interlayer bonding and entanglement may be enhanced by a thermo-mechanical process wherein the layered basesheet is passed between a heated smooth anvil roll and a heated pattern roll. The pattern roll may have any raised pattern which provides the desired entanglement and interlayer bonding. Desirably, the pattern roll defines a raised pattern which defines a plurality of bond locations which define a bond area of between about 4 and about 30 percent of the total area of the roll for improved interlayer attachment.

The basesheet for the wet wipes or wipe-type products may have a total basis weight of from about 25 to about 120 grams per square meter and desirably from about 40 to about 90 grams per square meter. Such basis weight of the layered basesheet may also vary depending upon the desired end use of the wet wipe or wipe-type products. For example, a suitable basesheet for wiping the skin may define a basis weight of from about 60 to about 80 grams per square meter and desirably about 75 grams per square meter. In a particular embodiment wherein the basesheet includes coform layers of polypropylene and cellulosic fibers and polyethylene and cellulosic fibers, the layered basesheet defines a basis weight of from about 60 to about 90 grams per square meter and desirably about 80 grams per square meter for improved softness and adequate strength.

In a particular embodiment, it is desired that the wet wipe of the present invention define sufficient strength to withstand the forces exerted by the user when it is wetted with solution. For example, the basesheet for the wet wipes or wipe-type products may define a tensile strength of at least about 1.23 Newtons per centimeter in the machine direction and at least about 0.70 Newtons per centimeter in the cross machine direction. The wipes or wipe-type having alternate ranges of tensile strength may also be effectively employed. As used herein, the term "machine direction" refers to the direction in which the material is manufactured while the cross machine direction refers to a direction which is perpendicular to the machine direction.

In a particular embodiment, wherein the basesheet includes coform layers of polypropylene and cellulosic fibers and polyethylene and cellulosic fibers, the layered basesheet defines a tensile strength of from about 1.31 to about 3.50 Newtons per centimeter in the machine direction and from about 0.84 to about 1.40 Newtons per centimeter in the cross machine direction and desirably from about 1.58 to about 1.93 Newtons per centimeter in the machine direction and from about 0.93 to about 1.11 Newtons per centimeter in the cross machine direction. In such a configuration, the coform layer which includes polypropylene fibers provides the majority of the strength to the basesheet while the coform layer which includes the polyethylene fibers provides a soft surface for contact with the skin of the user. Thus, the tensile strength of such a layered basesheet is higher than the tensile strength of a single layer containing polyethylene fibers and provides a softer surface than a single layer containing polypropylene fibers.

EXAMPLES

The following examples are presented to provide a more detailed understanding of the invention. The particular materials and parameters are exemplary and are not intended to limit the scope of the invention The following formulas are used in Examples 1–4:

|  | weight percent |
|---|---|
| Formula 1 | |
| Water | qs to 100% |
| Glycerin | 5% |
| Glyceryl stearate SE | 3% |
| Borage oil | 1% |
| Aloe | 0.3% |
| Tocopherol acetate | 0.3% |
| Suitable pH adjuster to pH 5.5 | |
| Formula 2 | |
| Water | qs to 100% |
| Glycerin | 5% |
| Glyceryl stearate SE | 3% |
| Borage oil | 1% |
| Aloe | 0.1% |
| Tocopherol acetate | 0.1% |
| PROLIPID 141, (International Specialty Products, Wayne, NJ) | 1% |
| Petrolatum | 1% |
| Soy sterol | 0.8% |
| Suitable pH adjuster to pH 5.5 | |
| Formula 3 | |
| Water | qs to 100% |
| Glycerin | 5% |
| Glyceryl stearate SE | 3% |
| Borage oil | 1% |
| Soy sterol | 0.8% |
| Aloe | 0.3% |
| Tocopherol acetate | 0.3% |
| Suitable pH adjuster to pH 5.5 | |
| Formula 4 | |
| Water | qs to 100% |
| Glycerin | 5% |
| Glyceryl stearate SE | 3% |
| Borage oil | 1% |
| Soy sterol | 0.8% |
| PROLIPID 141 (International Specialty Products, Wayne, NJ) | 1% |
| Aloe | 0.3% |
| Tocopherol acetate | 0.3% |
| Suitable pH adjuster to pH 5.5 | |
| Formula 5 | |
| Water | qs to 100% |
| Lipomicron NSLE, (Sederma, Le Perray-en-Yvelines, France) | 5% |

|  | weight percent |
|---|---|
| Formula 6 | |
| Water | qs to 100% |
| Glycerin | 5% |
| Sterol Esters | 0.5% |
| Petrolatum | 1% |
| Avocadin | 0.5% |
| PROLIPID 141 (International Specialty Products, Wayne, NJ) | 1% |
| Formula 7 | |
| Water | qs to 100% |
| Glycerin | 3.3% |
| Glyceryl stearate SE | 1.98% |
| Borage oil | 0.66% |
| Soy sterol | 0.53% |
| PROLIPID 141 (International Specialty Products, Wayne, NJ) | 0.66% |
| Aloe | 0.2% |
| Tocopherol acetate | 0.2% |
| Suitable pH adjuster to pH 5.5 | |

EXAMPLE 1

Lipid-enriched Wet Wipe Formulations Enhance Skin Barrier Against a Skin Irritating, Fecal Enzyme, Trypsin The EpiDerm™ skin model (Epi-200, Mattek Corporation, Ashland, Mass.) was used to assess the ability of the lipid-enriched wet wipe formulations to enhance skin barrier against permeation of trypsin (a skin irritating, fecal enzyme) and prevent a Interleukin-1α (IL-1α) response which is a measure of inflammation.

Test formulations (15 microliters) were added to the surface of the EpiDerm™ skin model and incubated for 30 minutes at 37° C., 5% $CO_2$ prior to dosing with the fecal enzyme, trypsin. The study was conducted using Epi-200 assay media devoid of hydrocortisone and pH indicator that was prepared by the manufacturer. After 30 minutes, the underlying media was removed and replaced with fresh, pre-warmed media followed by application of 10 microliters of 200 µg/ml of trypsin. The skin wells were incubated for 6 hours before the underlying media was removed and stored for further analysis. The media was assayed for permeated trypsin content using a fluorescent substrate (Boc-Gln-Ala-Arg-AMC.HCl, Bachem California Inc., Torrance, Calif.) specific to trypsin-like activity. Also, the amount of IL-1α in the media was measured using commercially available ELISA kits (Quantikine™ Human IL-1α Immunoassay, R&D Systems, Minneapolis, Minn.) specific for IL-1α to assess the ability of the formulations to prevent a pro-inflammatory response by the enzyme compared to the no treatment control.

TABLE 1.1

| Irritation: Pro-inflammatory Response (IL-1α) | |
|---|---|
| Treatment | Average IL-1α |
| PBS (control) | 25.8 |
| Trypsin | 108.7 |
| Formula 1 | 49.7 |
| Formula 2 | 70.0 |

TABLE 1.2

Permeated Trypsin

| Treatment | Average Permeated Trypsin (ng/ml) |
|---|---|
| PBS (control) | 0 |
| Trypsin | 802.5 |
| Formula 1 | 32.8 |
| Formula 2 | 105.6 |

Formula 1 and 2 enhanced the skin barrier of the Epi-Derm™ skin model against trypsin and reduced the pro-inflammatory response as measured by IL-1α after 6 hours compared to the trypsin control.

EXAMPLE 2

Lipid-enriched Wet Wipe Formulations Promote Barrier Repair as Measured by Transepidermal Water Loss (TEWL)

All studies were conducted in a temperature and humidity controlled room (71° F.±5° F.; 40±5% relative humidity).
2A. Twenty microliters of a wet wipe prototype formula was topically applied to the volar forearm of 24 female panelists following abrasion with emery cloth. TEWL measurements were obtained using a Dermalab evaporimeter pre- and post abrasion and 1,2, and 4 hours after application of the formulas. Mean TEWL values are expressed in Table 2.1. Repeated measures ANOVA was used to adjust for the repeated TEWL measures.

TABLE 2.1

TEWL (g/m²/hr) Results-Wet wipe formulations

| | Post Abrasion Mean | 1 Hour Mean | 2 Hour Mean | 4 Hour Mean |
|---|---|---|---|---|
| Formula 1 | 17.0 | 9.7* | 9.9* | 10.3 |
| Formula 3 | 15.5 | 8.7* | 8.4* | 8.2* |
| Formula 4 | 18.4 | 9.7* | 8.6* | 8.6* |
| Untreated | 17.4 | 12.7 | 12.0 | 11.5 |

*denotes significantly different than untreated site.

All lipid-enriched wet wipe formulations repaired the skin barrier compared to the untreated site at 1,2 and 4 hours after application of the formulas as measured by TEWL.
2B. Mean TEWL values following the same study design described above are expressed in Table 2.2. The pre-abrasion (baseline) TEWL values were subtracted from all of the other readings so as to correct for underlying subject-to-subject differences. All statistical evaluations were made on these differences.

TABLE 2.2

TEWL (g/m²/hr) Results-Wet wipe formulations

| | Post Abrasion Mean | 1 Hour Mean | 2 Hour Mean | 4 Hour Mean |
|---|---|---|---|---|
| Formula 5 | 12.0 | 6.4* | 5.6* | 5.1* |
| Formula 6 | 12.3 | 2.7*,** | 2.4*,** | 2.7*,** |
| Untreated | 11.5 | 9.9 | 9.6 | 10.0 |

*denotes significantly different than untreated site
**denotes significantly different than formula 5

Both formula 5 and 6 repaired the skin barrier compared to the untreated site as measured by TEWL. In addition, Formula 6 repaired the barrier significantly better than Formula 5. Formula 5 contains Lipomicron NSLE,a Sederma (Le Perray-en-Yvelines, France) product at the recommended use level that is marketed as a product for protection of the cutaneous barrier.

EXAMPLE 3

Lipid-enriched Wet Wipe Formulations Enhance Skin Moisturization as Measured by Conductance All studies were conducted in a temperature and humidity controlled room (71° F.±5° F.; 40±5% relative humidity).
3A. Twenty microliters of a wet wipe prototype was topically applied to the volar forearm. Conductance measurements were obtained using the Skicon instrument before application of the formulas and 1,2, 4, and 6 hours post application. Mean conductance values are expressed in Table 3.1. A pair-wise comparison for each time period using univariate ANOVAs was apppplied.

TABLE 3.1

Conductance-Wet wipe formulations

| | Baseline Mean | 1 Hour Mean | 2 Hour Mean | 4 Hour Mean | 6 Hour Mean |
|---|---|---|---|---|---|
| Formula 1 | 197.7 | 366.5* | 365.7* | 349.7* | 345.4* |
| Formula 3 | 182.8 | 298.6* | 297.5* | 311.5* | 304.6* |
| Formula 4 | 168.2 | 299.1* | 302.8* | 296.5* | 296.4* |
| Untreated | 164.3 | 178.3 | 176.9 | 175.0 | 176.3 |

*denotes significantly different than untreated site.

All wet wipe formulas significantly enhanced skin moisturization at 1, 2, 4 and 6 hours post application of the formulas compared to the untreated site.
3B. Mean Conductance values following the same study design described above with the exception that a conductance measure was not obtained at 6 hours post application are expressed in Table 3.2. The pre-application (baseline) conductance values were subtracted from all of the other readings so as to correct for underlying subject-to-subject differences. All statistical evaluations were made on these differences.

TABLE 3.2

Conductance-Wet wipe formulations

| | 1 Hour Mean | 2 Hour Mean | 4 Hour Mean |
|---|---|---|---|
| Formula 5 | 50.7 | 40.3 | 39.1 |
| Formula 6 | 194.0* | 166.6* | 142.2* |
| Untreated | 31.7 | 17.3 | 12.3 |

*denotes significantly different than untreated site.

Formula 6 significantly enhanced skin moisturization at 1, 2 and 4 hours post application of the formulas compared to the untreated site. Formula 5 failed to enhance skin moisturization at any of the times tested. Formula 5 contains Lipomicron NSLE,a Sederma (Le Perray-en-Yvelines, France) product at the recommended use level that is marketed as a product for protection of the cutaneous barrier.

EXAMPLE 4

Repetitive Wiping with Lipid-enriched Formulations on a Wet Wipe Basesheet Leaves Skin in a Natural Healthy State by not Damaging Skin Barrier All studies were conducted in a temperature and humidity controlled room (71° F.±5° F.; 40±5% relative humidity).

Wet wipes treated with lipid-enriched formulations were repeatedly rubbed on the volar forearm of 18 panelists in 4 cycles for a total of sixty times a day for the duration of four days. TEWL measurements were taken using the Dermalab evaporimeter at the beginning and end of each day. The table below shows the mean TEWL values at the beginning and completion of the study. Repeated measures ANOVA was used to adjust for the repeated TEWL measures.

TABLE 4.1

TEWL ($g/m^2/hr$) values at the beginning and end of the four day wiping cycle.

|  | Base Mean | End Day 4 Mean |
|---|---|---|
| Untreated | 6.5 | 4.7 |
| Formula 1 | 6.7 | 5.8* |
| Formula 3 | 6.6 | 5.1* |
| Formula 7 | 6.5 | 5.7* |

*denotes not significantly different than untreated.

Wet wipes that are treated with lipid-enriched formulations leave the skin in a natural, healthy state by not damaging skin barrier after repetitive wiping for the duration of four days.

Thus, the Examples representatively illustrate that the emulsion composition of the present invention may provide wet wipe or wipe-type products having improved skin health benefits as well as providing improved protection of the skin barrier function. Accordingly, the different aspects of the present invention can advantageously provide wet wipes or wipe-type products which, when compared to conventional wet wipes, have improved skin health benefits and protection of skin barrier function. Such wet wipes can advantageously be used for baby wipes, adult wipes, hand wipes, face wipes, cosmetic wipes, household wipes, industrial wipes and the like.

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A wet wipe or wipe-type product that enhances skin barrier having at least one layer and an oil-in-water emulsion composition comprising:
   from about 0.1 to about 30 weight percent of natural fats or oils;
   from about 0.1 to about 10 weight percent of sterol or sterol derivative;
   from about 0.1 to about 30 weight percent of humectant;
   from about 0.5 to about 20 weight percent of emulsifying surfactant having an HLB range from about 7 to about 18; and,
   from about 45 to about 99.5 weight percent of water.

2. The product of claim 1, wherein said water is a mixture of alcohol and water.

3. The product of claim 2, wherein said alcohol is less than about 70 weight percent of said alcohol and water mixture.

4. The product of claim 1, wherein said emulsion composition has a pH ranging from about 4 to about 7.

5. The product of claim 1, wherein the amount of said oil-in-water emulsion composition contained within each said wet wipe or wipe-type product is from about 150 to about 600 weight percent based on the weight of said product.

6. The product of claim 1, wherein said natural fat or oil is borage oil.

7. The product of claim 1, wherein said natural fat or oil is avocado oil.

8. The product of claim 1, wherein said natural fat or oil is sunflower oil.

9. The product of claim 1, wherein said sterol or sterol derivative is soy sterol.

10. The product of claim 1, wherein said sterol or sterol derivative is avocado sterols.

11. The product of claim 1, wherein said sterol or sterol derivative is cholesterol.

12. The product of claim 1, wherein said humectant is glycerin.

13. The product of claim 1, wherein said humectant is sorbitol.

14. The product of claim 1, wherein said humectant is propylene glycol.

15. The product of claim 1, wherein said emulsifying surfactant is glyceryl stearate SE.

16. The product of claim 1, wherein said emulsifying surfactant is emulsifying wax NF.

17. The product of claim 1, wherein said emulsifying surfactant is propylene glycol oleate SE.

18. The product of claim 1, wherein said composition further comprises from about 0.1 to about 30 weight percent petrolatum or mineral oil.

19. An oil-in-water emulsion composition comprising from about 0.1 to about 30 weight percent of natural fats or oils, from about 0.1 to about 10 weight percent of sterol or sterol derivative, from about 0.1 to about 30 weight percent of humectant, from about 0.5 to about 20 weight percent of emulsifying surfactant having an HLB range from about 7 to about 18, and from about 45 to about 99.5 weight percent of water.

20. The composition of claim 19, wherein said water is a mixture of alcohol and water.

21. The composition of claim 20, wherein said alcohol is less than about 70 weight percent of said alcohol and water mixture.

22. The composition of claim 19, wherein said emulsion composition has a pH ranging from about 4 to about 7.

23. The composition of claim 19, wherein said natural fats or oils is selected from the group consisting of: avocado oil, apricot oil, babassu oil, borage oil, camellia oil, canola oil, castor oil, coconut oil, corn oil, cottonseed oil, evening primrose oil, hydrogenated cottonseed oil, hydrogenated palm kernel oil, maleated soybean oil, meadowfoam oil, palm kernel oil, phospholipids, rapeseed oil, palmitic acid, stearic acid, linoleic acid, stearyl alcohol, lauryl alcohol, myristyl alcohol, benenyl alcohol, rose hip oil, sunflower oil, soybean oil, and mixtures thereof.

24. The composition of claim 19, wherein said sterol or sterol derivative is selected from the group consisting of: cholesterol, sitosterol, stigmasterol, ergosterol, lanasterol, soy sterol, avocado sterols, cholesterol esters, sterol esters, avocadin, lanolin, and mixtures thereof.

25. The composition of claim 19, wherein the amount of said fats or oils is from about 0.5 to about 10 weight percent.

26. The composition of claim 19, wherein the amount of said natural fats or oils is from about 1 to about 5 percent.

27. The composition of claim 19, further comprising from about 0 to about 30 weight percent of petrolatum or mineral oil.

28. The composition of claim 19, wherein the amount of said emulsifying surfactant is from about 1 to about 15 weight percent.

29. The composition of claim 19, wherein the amount of said humectant is from about 0.5 to about 20 weight percent.

30. The composition of claim 19, comprising about 1 weight percent borage oil, about 0.8 weight percent soy sterol, about 5 weight percent glycerin, about 3 weight percent glyceryl stearate SE, and about 90.2 weight percent water.

31. The composition of claim 30, wherein said emulsion composition has a pH of about 5.5.

32. The composition of claim 19, comprising about 1 weight percent borage oil, about 0.8 weight percent soy sterol, about 5 weight percent glycerin, about 3 weight percent glyceryl stearate SE, about 1 weight percent petrolatum USP, about 1 weight percent of a mixture between about 3 to about 40% lecithin, between about 15 to about 30% glycerly monostearate, between about 15 to about 40% blend of palmitic and stearic acid, and between about 0 to about 30% maleated soybean oil, and about 88.9 weight percent water.

33. The composition of claim 32, wherein said emulsion composition has a pH of about 5.5.

34. The composition of claim 19, comprising about 0.5 weight percent Avocadin, about 0.5 weight percent sterol esters, about 5 weight percent glycerin, about 1 weight percent glyceryl stearate in the form of a mixture of between about 3 to about 40% lecithin, between about 15 to about 30% glyceryl monostearate, between about 15 to about 40% blend of palmitic and stearic acid, and between about 0 to about 30% maleated soybean oil, and about 92 weight percent water.

35. The composition of claim 34, wherein said emulsion composition has a pH of about 5.5.

36. The composition of claim 19, comprising about 10 weight percent sunflower oil, about 1 weight percent cholesterol, about 3 weight percent glycerin, about 5 weight percent emulsifying wax NF, and about 81 weight percent water.

37. The composition of claim 36, wherein said emulsion composition has a pH of about 5.5.

38. The composition of claim 19, comprising about 5 weight percent avocado oil, about 1 weight percent lanasterol, about 1 weight percent sorbitol, about 5 weight percent propylene glycol oleate SE, and about 88 weight percent water.

39. The composition of claim 38, wherein said emulsion composition has a pH of about 5.5.

40. The composition of claim 19, comprising about 10 weight percent palm kernel oil, about 1 weight percent lanasterol, about 15 weight percent hydrogenated starch hydrolysate, about 15 weight percent glyceryl stearate, about 5 weight percent petrolatum or mineral oil, and about 54 weight percent water.

41. The composition of claim 40, wherein said emulsion composition has a pH of about 5.5.

42. The composition of claim 19, comprising about 10 weight percent lanolin, about 5 weight percent soy sterol, about 5 weight percent glycerin, about 10 weight percent emulsifying wax NF, about 5 weight percent petrolatum or mineral oil, and about 60 weight percent water.

43. The composition of claim 42, wherein said emulsion composition has a pH of about 5.5.

44. The composition of claim 19, comprising about 15 weight percent cottonseed oil, about 15 weight percent sterol esters, about 10 weight percent propylene glycol, about 15 weight percent propylene glycol oleate SE, about 10 weight percent petrolatum or mineral oil, and about 45 weight percent water.

45. The composition of claim 44, wherein said emulsion composition has a pH of about 5.5.

46. The composition of claim 19, comprising about 30 weight percent evening primrose oil, about 5 weight percent cholesterol, about 5 weight percent sodium PCA, about 10 weight percent propylene glycol oleate SE, and about 50 weight percent water.

47. The composition of claim 46, wherein said emulsion composition has a pH of about 5.5.

48. A nonwoven wipe-type product that enhances skin barrier having an oil-in-water emulsion composition comprising:

from about 0.1 to about 30 weight percent of natural fats or oils;

from about 0.1 to about 10 weight percent of sterol or sterol derivative;

from about 0.1 to about 30 weight percent of humectant;

from about 0.5 to about 20 weight percent of emulsifying surfactant having an HLB range from about 7 to about 18; and, from about 45 to about 99.5 weight percent of water.

49. The product of claim 48, wherein said emulsion composition has a pH ranging from about 4 to about 7.

50. The product of claim 48, wherein said water is a mixture of alcohol and water.

51. The product of claim 50, wherein said alcohol is less than about 70 weight percent of said alcohol and water mixture.

\* \* \* \* \*